(12) United States Patent
Kalergis et al.

(10) Patent No.: US 9,849,141 B2
(45) Date of Patent: Dec. 26, 2017

(54) USE OF SPIRONOLACTONE-BASED COMPOSITION THAT EXHIBITS AN INHIBITORY ACTION ON T-LYMPHOCYTE ACTIVATION WHICH IS USEFUL FOR PREVENTING AND/OR TREATING MULTIPLE SCLEROSIS

(71) Applicant: PONTIFICIA UNIVERSIDAD CATOLICA DE CHILE, Santiago (CL)

(72) Inventors: Alexis M. Kalergis, Santiago (CL); Andres A. Herrada, Santiago (CL)

(73) Assignee: PONTIFICIA UNIVERSIDAD CATOLICA DE CHILE (CL)

( * ) Notice: Subject to any disclaimer, the term of this patent is extended or adjusted under 35 U.S.C. 154(b) by 403 days.

(21) Appl. No.: 14/104,799

(22) Filed: Dec. 12, 2013

(65) Prior Publication Data
US 2014/0099367 A1   Apr. 10, 2014

Related U.S. Application Data

(63) Continuation of application No. 13/881,125, filed as application No. PCT/IB2011/054397 on Oct. 6, 2011, now abandoned.

(30) Foreign Application Priority Data

Oct. 26, 2010   (CL) .................................. 1174-2010

(51) Int. Cl.
A61K 31/585   (2006.01)

(52) U.S. Cl.
CPC .................................. A61K 31/585 (2013.01)

(58) Field of Classification Search
CPC .................................................... A61K 31/585
See application file for complete search history.

(56) References Cited

U.S. PATENT DOCUMENTS

2010/0119582 A1* 5/2010 Boerger et al. ............... 424/426

OTHER PUBLICATIONS

Merten et al., Pilot Study on the Efficacy of High Doses of Aldosterone and Spirolactone Derivatives in the Treatment of Multiple Sclerosis, Z. Neurol., 202:217-228, 1972.*
Mertin et al. Translation.*
Liu et al., Effects of spironolactone on systolic blood pressure in experimental diabetic rats, Kidney International, vol. 57:2064-2071, 2000.*
Nash et al., High-dose immunosuppressive therapy and autologous peripheral blood stem cell transplantation for severe multiple sclerosis, Blood, 102(7):2364-2372, 2003.*
Liang et al., CdSe quantum dots as luminescent probes for spironolactone determination, Talanta, 69:126-130, 2006.*

Aharoni et al. "Demyelination arrest and remyelination induced by glatiramer acetate treatment of experimental autoimmune encephalomyelitis." PNAS. 105(32):11358-11363. 2008.
Bolland et al. "Genetic Modifiers of Systemic Lupus Erythematosus in FcγRIIB-/-Mice" J. Exp. Med. 195(9):1167-1174. 2002.
Goodin et al. "Assessment: The use of natalizumab (Tysabri) for the treatment of multiple sclerosis (an evidence-based review)." Neurology. 71:766-773. 2008.
Herrada et al. "Aldosterone Promotes Autoimmune Damage by Enhancing Th17-Mediated Immunity." J. of Immunology. 184:191-202. 2010.
Hofmann et al. "Comparison of Spironolactone Tablet Dosage Forms in Healthy Humans." J. of Pharm. Sci. 63(8):1248-1253. 1974.
International Search Report for International Application No. PCT/IB2011/054397 dated Mar. 1, 2012 (3 pages).
Liang et al. "CdSe quantum dots as luminescent probes for spironolactone determination." Talanta. 69:126-130. 2006.
Liebich et al. "Summary: Alterations of lymphocytes by aldosterone and potassium canrenoate: experimental and clinical investigations." Fortschr. Med. 100(41):1992-1925. 1982.—Abstract Only.
Mertin et al. "Pilot Study on the Efficacy of High Doses of Aldosterone and Spirolactone Derivaties in the Treatment of Multiple Sclerosis." Z. Neurol. 202:217-228. 1972.
Montu et al. "Mixtoxantrone in secondarily progressive multiple sclerosis: a series of 18 patients." Neuroligia. 18(6):318-323. 2003.
Pitt et al. "The Effect of Spronolactone on Morbidity and Mortality in Patients with Severe Heart Failure." The New England J. of Med. 341(10):709-717. 1999.
Skihar et al. "Promoting oligodendrogenesis and myelin repair using the multiple sclerosis medication glatiramer acetate." PNAS. 106(42):17992-17997. 2009.
Trachtman et al. "Prevention of renal fibrosis by spironolactone in mice with complete unilateral ureteral obstruction." J. of Urology. 172:1590-1594. 2004.
Unknown. "Atlas Multiple Sclerosis Resources in the World 2008" World Health Organization. 2008. pp. 1-51.
Winnewisser et al. "Lympocyte Stimlation with PHA under Combined Therapy with Aldosterone and Sprolactone Derivaties." Klin. Wschr. 51:286-287. 1973.

* cited by examiner

Primary Examiner — James D. Anderson
(74) Attorney, Agent, or Firm — Merchant & Gould P.C.

(57) ABSTRACT

The present invention relates to the use of spironolactone for the preparation of a pharmaceutical composition intended for preventing and/or treating multiple sclerosis. Alternatively, the invention relates to the use of spironolactone directly in T-lymphocytes or dendritic cells obtained from a blood sample taken from a patient and then injected back into the circulation. Therefore, the present invention relates to the use of a composition comprising spironolactone that can be used in the treatment of multiple sclerosis, which covers the administration of spironolactone directly or lymphocytes pre-treated with spironolactone, or dendritic cells to individuals requiring such treatment. Spironolactone is an orally administered drug that is less expensive than many of the treatments available for MS and, furthermore, has the advantage of being a known compound already used in humans for extended periods and therefore the adverse effects thereof have been described in clinical studies.

7 Claims, 5 Drawing Sheets

Figure 4
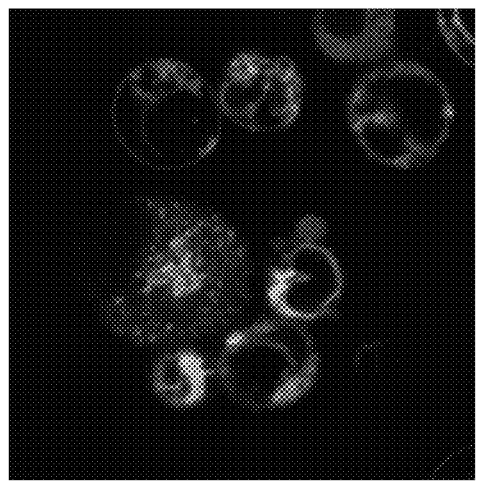
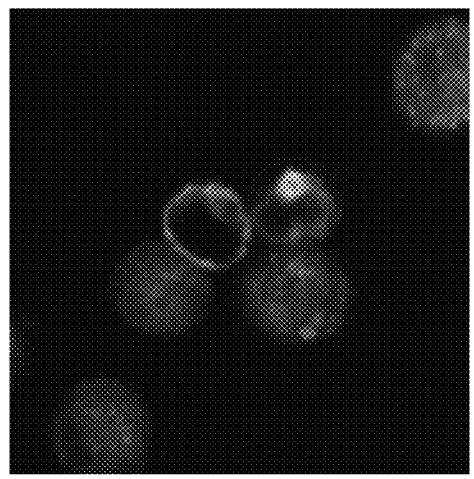

USE OF SPIRONOLACTONE-BASED COMPOSITION THAT EXHIBITS AN INHIBITORY ACTION ON T-LYMPHOCYTE ACTIVATION WHICH IS USEFUL FOR PREVENTING AND/OR TREATING MULTIPLE SCLEROSIS

This application is a Continuation of U.S. Ser. No. 13/881,125 filed 23 Apr. 2013, which is a National Stage Application of PCT/IB2011/054397, filed 6 Oct. 2011, which claims benefit of Serial No. 1174-2010, filed 26 Oct. 2010 in Chile and which applications are incorporated herein by reference. To the extent appropriate, a claim of priority is made to each of the above disclosed applications.

FIELD OF INVENTION

The present invention relates to the use of a composition comprising spironolactone for the treatment of multiple sclerosis.

BACKGROUND OF THE INVENTION

Multiple Sclerosis (MS) is one of the most common neurological disorders worldwide and one of the major neurological non-traumatic disability causes in young adults, more common in women than men, the first symptoms appearing around 30 years of age. Multiple sclerosis is a progressive disease, of autoimmune inflammatory origin, characterized by the loss or damage of myelin sheath coating nervous fibers of the Central Nervous System (CNS), which is substituted with connective tissue plaques. This generates an alteration in conduction of nervous impulse and said alteration is the source of the most common symptoms of the disease, such as muscular weakness, spasticity or motor dysfunction, visual alterations, equilibrium problems, urinary dysfunction, constipation, and cognitive or behavioral anomalies (Atlas multiple sclerosis resources in the World. World Health Organization, 2008). The course of the disease is presented with periods of outbreaks alternated with periods of remission of undefined duration. It has been shown that T-lymphocytes play an important role during the beginning and development of the disease. T-lymphocytes are immune system cells responsible of coordination of an adaptive immune response against specific antigens. Normally, during an infection situation of the organism, immune system cells known as antigen-presenting cells, capture and phagocyte the pathogen agent, degrading and exposing its antigens on their surface through the linkage to the Major Histocompatibility Complex (MHC). These cells migrate and move towards T-lymphocytes in lymph nodes or spleen, searching for T-lymphocytes exerting an specific response to the invasive pathogen. This search is made through the interaction between the peptide derived from the pathogen bound to the MHC of the antigen-presenting cell with the T-lymphocyte Receptor (TCR) expressed on the surface of each T-lymphocyte, wherein all TCR have a unique and different specificity for each of the T-lymphocytes. In this manner, when a T-lymphocyte specifically recognizes the pathogenic peptide bound to the MHC, receives positive signals that induce multiplication of this specific T-lymphocyte, in order to generate a suitable number to fight the pathogen. Finally, T-lymphocytes migrate to the infection sites, and, through different mechanisms, achieve the elimination of the infective agent, reestablishing the homeostasis in the organism. Nevertheless, in certain occasions, T-lymphocytes recognize self-antigens, as the case maybe of antigens derived from the myelin sheath from oligodendrocytes, presented in MHC in antigen-presenting cells, generating now an activation of self-reactive T-lymphocytes which will attack specifically the myelin sheath and therefore, initiate the development of MS. Therefore, an effective treatment against this autoimmune disease requires control over activation of self-reactive T-lymphocytes.

Currently, available treatments for MS include drugs with the objective of reducing activity of the disease and modification of its natural course, as well as addressing the symptoms generated by the disease, such as pain, intestinal and urinary problems, sensorial problems, fatigue and others. Among the most common methods of treatment for MS, which have as an objective modifying the course of the disease or its activity, are the treatment with Interferon beta (INF-$\beta$), mitoxantrone and glatiramer acetate (Atlas MS resources in the World. WHO 2008). Type 1 Interferon-beta (T1INF-$\beta$) is commonly the first election treatment. The mechanism of action of T1INF-$\beta$, allowing the reduction of the incidence of outbreaks in MS patients, is not clear. T1INF-$\beta$ is a native cytokine whose principal function is accentuating the antiviral immunity of T-cells and it has been proposed that T1INF-$\beta$ stimulates innate immunity conditioning myeloid dendritic cells, a type of antigen-presenting cells, which promote expansion and function of regulatory natural killer T cells (iNKT). Said regulatory iNKT would impede the T-cell effector response in zones where autoimmunity occurs in patients suffering MS. Meanwhile, mitoxatrone is a immunosuppressant drug which was originally used as an antineoplastic agent. Mitoxatrone reduces the number of T-cells, suppresses humoral immunity and produces an inhibition of suppressor T-cells. Mitoxantrone has shown to be useful in reducing the number of outbreaks and progression of incapacity produced by MS (Pericot & Montalban 2003, Neurologia, 18(6):318-323). Glatiramer acetate (also known as copolymer 1), another of treatment methods for MS, is an immunomodulator agent and it has been suggested that it acts by reducing inflammation and promoting oligodendrogenesis and re-myelinization. This suggestion is based on the results obtained in studies performed on an experimental model of autoimmune encefalomyelitis in mice (animal model of MS disease), which show that glatiramer acetate allows an increase in proliferation, differentiation and survival of oligodendrocytes, which relates to an increase of them in damaged sites and thus, allowing in situ reparation processes (Aharoni et al. 2008, PNAS, 105(32): 11358-11363). It has also been proposed that this increase would be triggered by an increase of certain growth factors, such as insulin-like growth factor (IGF-1) and brain derived neurothrophic factor (BDNF) generating a decrease on the symptoms of the disease.

Apart from the three mentioned drugs, other drugs exist used or proposed to be used for the treatment of MS with the objective of modifying the course of the disease. One of them is natalizumab (Tysabri), which is a monoclonal antibody binding to $\alpha 4$ subunit of $\alpha 4\beta 1$ and $\alpha 4\beta 7$ integrins which are expressed, among other places, in the surface of activated T-lymphocytes, avoiding that said T-lymphocytes migrate through the blood-brain barrier to the central nervous system (CNS). Also, natalizumab suppresses in course inflammatory reactions, inhibiting the union of $\alpha 4$ positive leucocytes to osteopontin and fibronectin, which in turns decreases the number of white blood cells in the brain-spinal fluid compared to a non-treated patient. On the other hand, it has been proposed that the use of statins, particularly atorvastatin, which is an agent with cholesterol reducing properties, and which is used in the treatment of cardiovascular diseases, could have a role in suppressing MS. This would be explained since statins, as part of their cholesterol reducing function, would also have the capacity to suppress the activation of T-cells and induction of expression of class II MHC in antigen-presenting cells, thus reducing the immune response. Also, cyclophosphamide has been used as a non-specific immunosuppressant, which has proved to reduce the activity of the disease and the incapacity in a high percentage of patients, without grave side effects.

In spite of the multiple drugs previously described, many MS patients do not respond in a favorable way, either because they have no significant effect on the course of the disease or because they show important side effects. Also, the majority of drugs used up until now, are parenteral drugs, which would imply a higher complexity and discomfort for its application. Therefore, it is necessary to have new treatments modifying the course and progression of the disease and, preferentially, allowing the oral administration of the pharmaceutical composition. Therefore, the objective of our invention is providing a new method for the treatment of MS addressing the abovementioned issues.

SUMMARY OF THE INVENTION

The present invention relates to the use of spironolactone for the preparation of a pharmaceutical composition intended for preventing and/or treating multiple sclerosis. Alternatively, the invention relates to the use of spironolactone directly in T-lymphocytes or dendritic cells obtained from a blood sample taken from a patient and then injected back into the circulation. Therefore, the present invention relates to the use of a composition that comprises spironolactone that can be used in the treatment of multiple sclerosis, which covers the administration of spironolactone directly or of T-lymphocytes pre-treated with spironolactone, or dendritic cells to individuals requiring such treatment. Spironolactone is an orally administered drug that is less expensive than many of the treatments available for MS and, furthermore has the advantage of being a known compound already used in humans over extended periods and therefore the adverse effects thereof have been described in clinical studies.

DESCRIPTION OF FIGURES

FIG. 4: Photographs using confocal fluorescence microscopy, showing immunological synapsis between antigen-presenting dendritic cells and T-lymphocyte. T-lymphocytes were dyed with BODIPY FL C5-Ceramide, which is directed to the Golgi apparatus, while antigen-presenting cells were dyed with CMTMR-Orange and co-cultured without spironolactone (FIG. 4A) or in the presence of spironolactone (FIG. 4B) during 2 hrs, afterwards, the cells were observed under a confocal fluorescence microscope.

DETAILED DESCRIPTION OF THE INVENTION

Figure 1:
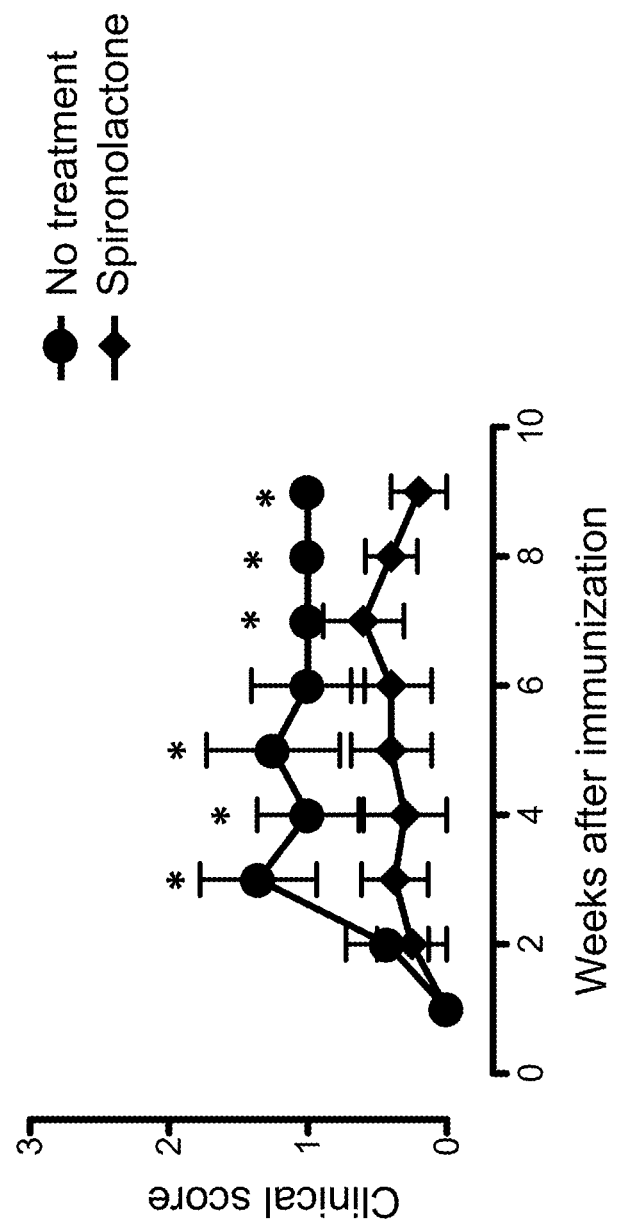
FIG. 1. Plot showing the effect of a composition comprising spironolactone in the treatment of progression of damage associated to Multiple Sclerosis. C57BL/6 female mice of 6 to 8 weeks were EAE induced and then separated in 2 groups. The control group was fed with standard pellet food (-●-). The other group of mice was fed with the same type of pellets as the control group, supplemented with 1.8 mg of spironolactone as daily dose per mouse (-♦-). Y-axis corresponds to the clinical score and X-axis shows time in days, wherein day 0 corresponds to day 15 after sensibilization. Clinical signs of disease were observed according to the following criteria: 0, no sign of immune damage; 1: dropped tail; 2: back paws weakness and abnormal walking; 3: complete paralysis of back paws; 4: front paws paralysis; 5: death.

The present invention is based in the determination of a therapeutic effect of a composition comprising spironolactone that was not previously described. Spironolactone is a synthetic steroid with a structure similar to aldosterone.

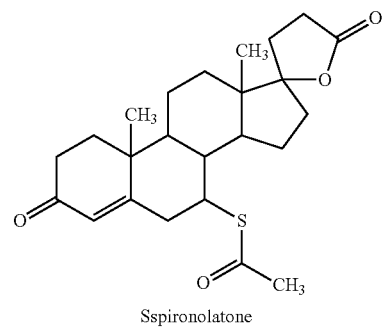 [SMILES: CC(=O)SC1CC2=CC(=O)CCC2(C)C2CCC3(C)C(CCC34CCC(=O)O4)C12]

Sspironolatone

Spironolactone binds to the mineralocorticoid receptor (MR) inhibiting competitively the action of aldosterone, which is why it has been used for over 40 years for the treatment of hyperaldosteroinism. For the same reason it has been used for inhibiting the pathophysiological action of aldosterone in cardiac failure (Pitt et al. 1999. The New England Journal of Medicine, 341(10): 709-717).

The objective in determining if a composition of spironolactone would have an effect in the development of MS is based on the results obtained from a research from our group, relating to the mechanism of action of aldosterone for generating hypertension and cardiovascular disease (Herrada et al. 2010. Journal of Immunology, 184, 191-202). Aldosterone is a mineralocorticoid hormone involved in regulation of the concentration of blood electrolytes and physiological volume homeostasis, processes that require interaction of aldosterone with MR. The excessive production of aldosterone conducts to the development of hypertension and cardiovascular disease. It has been suggested that these diseases could have their origin in an inflammatory effect caused by aldosterone, promoted by immunity mediated through T-cells. Therefore, our research had as an objective to evaluate if aldosterone could modulate the function of dendritic cells, an antigen-presenting cell type, which control the nature and intensity of the response from T-cells. The results from our experiments show that dendritic cells stimulated with aldosterone induce the T helper 17 (Th17) phenotype in CD4+ T-cells, a phenotype that in recent studies has been associated with promotion of inflammatory and autoimmune diseases. The activator effects of aldosterone in the function of dendritic cells could be suppressed by epleronone and spironolactone, both RM inhibitors. Consistently, experimental autoimmune encefalomyelitis mice (EAE, experimental animal model for MS), an autoimmune disease promoted by Th17 cells, showed a deterioration in their disease with the administration of aldosterone. Nevertheless, when using MR inhibitors in EAE mice, only spironolactone had protecting effects even in EAE mice that did not received aldosterone. From these observations, we decided to study the effect of a spironolactone composition in multiple sclerosis.

In our studies, we demonstrated that a spironolactone composition is useful in the treatment of MS, but it is not effective in other diseases of autoimmune origin, such as systemic lupus erythematosus (SLE). Therefore, we propose the use of a spironolactone composition for the treatment and/or prevention of multiple sclerosis. Spironolactone can be used in the fabrication of a pharmaceutical composition useful for administration to a patient with MS for the treatment of the disease. The pharmaceutical composition can be in different forms of dosage, such as dose directed to parenteral administration or dose directed to oral administration or any other suitable form. In the case of parenteral administration, the dosage form can correspond to an injectable liquid or a powdered preparation that can be reconstituted in liquid, prior to parenteral administration, or it can also be in the form of an implantable device or pellet suitable for prolonged release of the active ingredient. Preferentially, it is suggested the use of a spironolactone composition for preparation of a medicine for oral administration directed to the treatment of MS, which comprises spironolactone as active ingredient, in either of its pharmaceutically acceptable forms, and suitable excipients for oral administration. The pharmaceutical form can be a coated or non-coated tablet, hard or soft capsules, powders, granules, pills, or other suitable pharmaceutical form for spironolactone administration. Alternatively, the use of a spironolactone composition in the treatment of T-cells or dendritic cells directly obtained from the blood of patients suffering MS is proposed. Afterwards, said treated lymphocytes or dendritic cells can be returned to patients circulation to exert their effect in the treatment of MS. This route would avoid the use of spironolactone directly in the patient, which would avoid potential adverse side effects of spironolactone and would allow a more specific and direct response of a spironolactone composition over T-lymphocytes.

The administration dose should be adjusted for the requirement of the individual in need. It is known that in humans the administration of 25 to 50 mg of spironolactone daily for the treatment of cardiac failure and from 100 to 400 mg daily for the treatment of hyperaldosteronism. Therefore, the use of spironolactone in the range from 25 to 400 mg has been already studied in regard to the potential adverse effects that it could have. For the treatment of multiple sclerosis we propose to adjust a dose in the disclosed range for humans, i.e. the dose should be in the range of 25 to 400 mg daily.

As used in the present document, the term "pharmaceutically acceptable" is referred to compounds, materials, compositions, and/or dosage forms that, inside the medical-pharmaceutical good judgment, are suitable for contacting mammal tissues, particularly human, without an excessive toxicity, irritation, allergic reactions, or other problematic complications, in a commensurate manner with a reasonable benefit/risk ratio. In the case of treatment through lymphocytes or dendritic cells obtained from peripheral blood from patients, the dose should be approximately between 2 to 10 ugr/ml spironolactone for every 100,000-1,000,000 cells, over 24 hour period. Preferentially, the dose can be 5 ugr/ml spironolactone for every 100,000-1,000,000 cells, just as it is described in our research. Afterwards, cells must be washed in order to remove the spironolactone excess, and inject them back to the patient's blood. Obtaining T-lymphocytes or dendritic cells from peripheral blood can be performed using any method described for the separation of T-lymphocytes from a blood sample. As an example, it is below described, a form of obtaining and treating T-lymphocytes from a patient. A sample of blood is collected, approximately 10 to 50 ml through venipuncture, disposing the blood in heparinized tubes. White cells, containing T-lymphocytes, are obtained through density separation in a Ficoll gradient, slowly depositing blood over Ficoll gradient. After centrifuging at 300 G for 25 minutes at 20° C., the white cells ring is withdrawn, which is easily distinguishable from red cells. These cells, containing in a great proportion T-lymphocytes, are washed with PBS and incubated in the presence of spironolactone in X-VIVO 15 medium, during 24 hours at 37° C. in a culture chamber. Once the incubation is finished, these cells are washed again with PBS, and are injected intravenously to the patient.

Animal Model of Multiple Sclerosis, Experimental Autoimmune Encefalomyelitis.

The animal model used for the study of the effect of a composition of spironolactone in MS is experimental autoimmune encefalomyelitis or experimental allergic encefalomyelitis (EAE). EAE is the most used experimental animal model for MS study, since both have an autoimmune origin and share similar pathologic features, such as propagated demyelinization (Aharoni et al. 2008, PNAS, 105(32): 11358-11363). This animal model has allowed the development of two of the most currently used approved therapies for MS: mitoxantrone and glatiramer acetate, besides the therapy comprising administration of monoclonal antibody natalizumab.

In our study, we have used C57BL/6 female mice of 6 to 8 weeks old, to which EAE was induced through injection of 50 µg of MOG 35-55 peptide (Myelin Oligodendrocyte Glycoprotein) supplemented with heat inactivated *Mycobacterium tuberculosis* H37 Ra. MOG peptide mimics the proteins expressed in the myelin sheath, while a *Mycobacterium tuberculosis* extract, being a pathogen agent, generates inflammation of tissues and further recruitment of antigen-presenting cells, therefore facilitating the capture of MOG and presentation of this antigen to auto reactive T-lymphocytes, in order to produce their activation. At the same moment, 500 ng of Pertussis toxin was administered intraperitoneally, which was repeated after 48 hours, in order to permeabilize the blood-brain barrier, thus allowing the passage of auto reactive T-lymphocytes to CNS and thus allowing the attack of myelin sheath generating the disease. Usually, clinical EAE symptoms appear between 15 to 18 days from the moment the disease was induced. In order to determine the evolution of the disease, a clinical score is used, based on the motor symptoms. The considered variables and the corresponding clinical score are indicated in the following table:

| Variable | Clinical Score |
| --- | --- |
| No detectable signs of disease | 0 |
| Presence of dropped tail | 1 |
| Back paws weakness and abnormal walking | 2 |
| Complete paralysis of back paws | 3 |
| Front and back paws paralysis | 4 |
| Death | 5 |

Effect of a Spironolactone Composition in EAE Mice

EAE induced mice, according to the previously described method, were separated in two groups. One of them, the control group, was fed with standard pellets in a daily ration of 3 gr. The other group was fed with the same kind of pellets and ration than the control group, but the pellets were supplemented with a spironolactone composition in a daily dose of 1.8 mg per mouse. Our results show that the use of a spironolactone composition, significantly reduces the clinical score associated with the disease (FIG. 1). Therefore, our data show that spironolactone acts as an autoimmune damage, generated by EAE, suppressant.

Spironolactone Mechanism of Action

Figure 2:
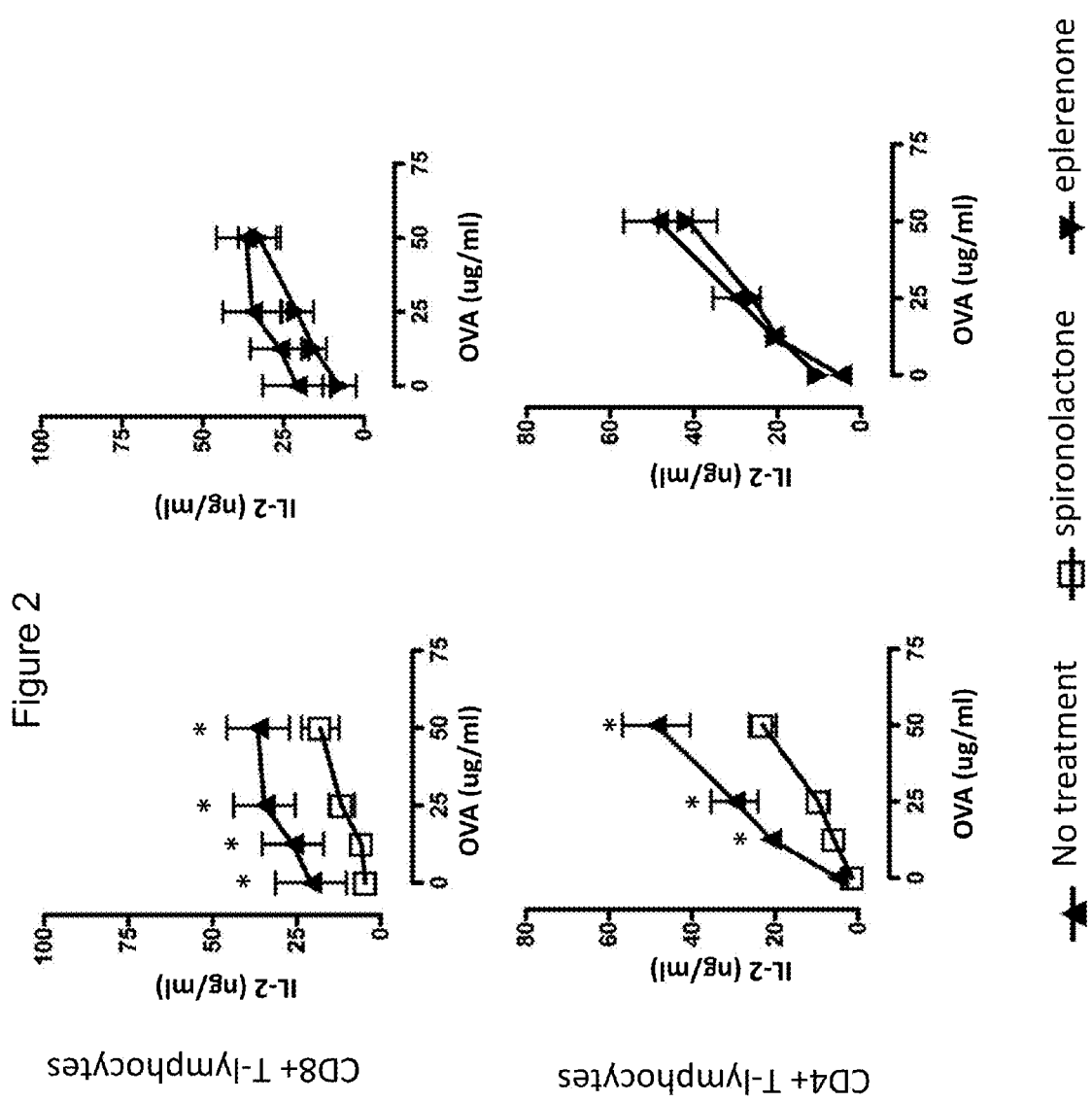
FIG. 2. Plots showing the effect of a composition comprising spironolactone in the inhibition of activation of T-lymphocytes through antigen-presenting cells. Antigen-presenting cells (dendritic cells) were pulsed with ovalbumin, washed and co-cultured with CD8+ or CD4+T-lymphocytes obtained from transgenic mice whose TCR specifically recognizes an ovalbumin derived peptide charged on class I or II MHC respectively. At the same time, the culture was treated with spironolactone (-□-) eplerenone (-▼-) or not treated (control -▲-) and after 24 hours, the supernatant was withdrawn and the presence of interleukin-2 (IL-2) assayed using ELISA. *p<0.05 one-way ANOVA.

Antigen-presenting cells were pulsed with 10 ug/ml of ovalbumin (OVA) protein over 24 hrs, washed and then co-cultured with CD8+ or CD4+T-lymphocytes obtained from transgenic mice whose TCR recognizes specifically a ovalbumin derived peptide charged in MHC class I or II, respectively. A group of cells was treated with 5 ug/ml spironolactone during co-culture, other group was treated with 5 ug/ml epleronone, other drug which has been described as specific blocker of mineralocorticoid receptor, and the control group did not receive any additional treatment. After 24 hrs, the supernatant was withdrawn and IL-2 secretion, a cytokine secreted by activated T-lymphocytes, was assayed using ELISA assay. In this specific immunological test, it is expected the activation of said T-lymphocytes and, therefore, an increase in IL-2 secretion. Nevertheless, we observed that the spironolactone treatment, during co-culture, inhibits the activation of T-lymphocytes (FIG. 2). This inhibiting effect of spironolactone would not simply obey to the blocking of the mineralocorticoid receptor, but rather to an undetermined mechanism, since when using another mineralocorticoid receptor inhibitor, epleronone, no such inhibiting effect on the activation of T-lymphocytes is observed.

Figure 3:
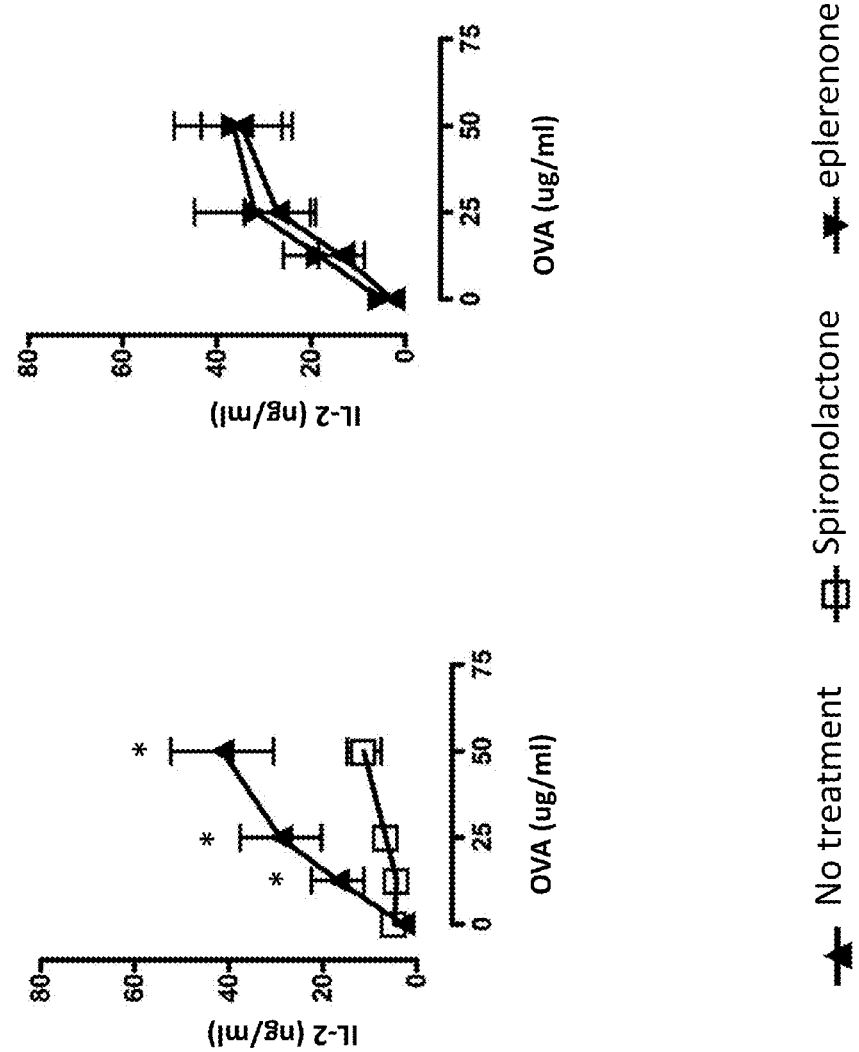
FIG. 3: Plots showing the effect of a composition comprising spironolactone or eplerenone in the activation of T-lymphocytes independent from antigen-presenting dendritic cells. An ELISA plate was activated with different concentrations of anti-CD3ε overnight, and then purified CD8+ T-lymphocytes were added and treated for 24 hrs with spironolactone (-□-), eplerenone (-▼-) o not treated (control -▲-). When the time was completed the supernatant was extracted and the IL-2 levels were determined using ELISA.

The following experiment was made in order to determine if spironolactone acts directly on T-lymphocytes or the effect is on the function of antigen-presenting cells. An ELISA plate was activated with different concentrations of anti-CD3ε overnight, and then, purified CD8+T-lymphocytes were added and treated with either spironolactone or epleronone (5 ug/ml) during 24 hrs. After that period, the supernatant was withdrawn and IL-2 levels were determined using ELISA. This assay is based on that T-lymphocytes, beside expressing TCR, express a protein denominated CD3, which transduces the activating signal, generated by the interaction of TCR with the antigenic peptide bound to the MHC of the antigen-presenting cell, to the interior of the T-lymphocyte. When the experiment was performed, we observed the same inhibiting effect on the secretion of IL-2 due to spironolactone, which demonstrates that spironolactone has a direct blocking effect on the activation of T-lymphocyte and not only on the antigen-presenting cell (FIG. 3).

In order to complement these results, the direct effect of spironolactone on the interaction between T-lymphocytes and antigen-presenting cells was studied. It has been determined that an efficient activation of T-lymphocytes requires an stable interaction between the antigen-presenting cell and the T-lymphocyte, which is known as "immune synapsis". A stable immune synapsis is translated in a polarization of the Golgi apparatus, an organelle in charge of protein transport, of the T-lymphocyte towards the contacting site with the antigen-presenting cell. In this way, it is possible to observe an efficient immune synapsis checking if a polarization from Golgi apparatus towards the contacting site with the antigen-presenting cell exists or not. To observe if the spironolactone treatment generated any alteration in the immune synapsis, T-lymphocytes were treated for 30 minutes with a green dye (BODIPY FL C5-Ceramide) which specifically dyes Golgi apparatus, while antigen-presenting cells pulsed with ovalbumin were dyed red (CMTMR-Orange). Afterwards, both cell groups were contacted and the interaction between cells using a confocal fluorescence microscope was observed. An immune synapsis can be observed when contacting antigen-presenting cells pulsed with ovalbumin with transgenic T-lymphocytes whose TCR recognizes this protein, characterized by a polarization of the green label of the T-lymphocyte, reflecting the Golgi apparatus, towards the antigen-presenting cells which are dyed in red (FIG. 4A). Nevertheless, if 5 ug/ml of spironolactone are added to the culture medium, this polarization of the Golgi apparatus of the T-lymphocyte towards the antigen-presenting cell is not observed and therefore, immune synapsis is not produced (FIG. 4B). In this way, it is possible to conclude that blocking the activation of T-lymphocytes with spironolactone would be due to the lack of interaction of auto reactive T-lymphocytes and antigen-presenting cells, which produces an inhibition of T-lymphocytes, turning this inhibition in an adaptive cell response directed to the myelin sheath, which would be reflected in the inhibition of the autoimmune damage associated to EAE and therefore in multiple sclerosis.

Effect of Spironolactone in Systemic Lupus Erythematosus.

Figure 5:
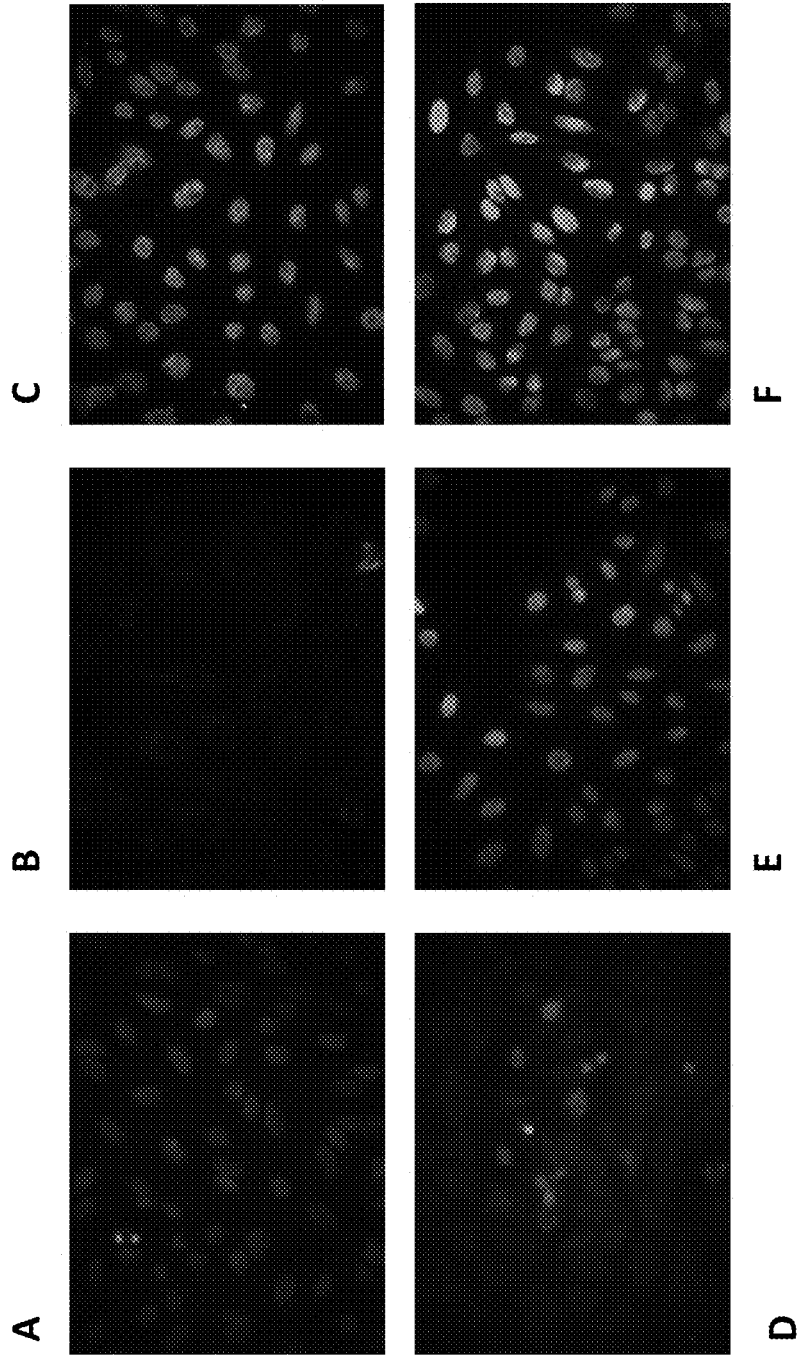
FIG. 5: Photographs using confocal fluorescence microscopy, showing the effect of a composition comprising spironolactone in the progression of systemic lupus erythematosus. Knockout mice for FcRIIb receptor developing systemic lupus erythematosus (SLE) spontaneously, were treated with standard pellets supplemented with 1.8 mg spironolactone orally in a daily dose (FIGS. 5D-5F), or fed with only standard pellets (FIGS. 5A-5C). The images correspond to fluorescence microscope photographs for anti-nuclear antibodies at 2 months (Figures A and D), 4 months (figures B and E) and 8 months (Figures C and F) with n=6 for each treatment.

It is possible, based on the prior information, to consider that spironolactone could act attenuating in general any symptom related with autoimmune pathologies. In order to answer this question, we wanted to determine the effect of administering a spironolactone composition in another autoimmune disease currently of great importance, systemic lupus erythematosus. This disease is characterized by the attack of the immune system cells to different organs, such as skin, joints, kidney, cardiovascular system, among others, due to the aggregation of immune complexes in these organs. Our studies were made in FcγII receptor knockout mice, a receptor which is expressed in many immune cells, and whose absence generates a systemic lupus erythematosus-like disease spontaneously (Bolland et al; J. Exp. Med., May 2002; 195: 1167). When these mice were treated with spironolactone in the same manner as the previously described experiments, we did not observe a decrease in the deposition of immune complexes in the kidney of mice, a measurement parameter of damage generated by lupus, compared to regularly fed mice (FIG. 5). A possible explanation is that, a key role in lupus pathology is played by B-lymphocytes, cells in charge of antibody production, whose excess production generates the antigen-antibody complexes deposits in different target organs, generating inflammation and autoimmune damage associated with lupus. Instead in MS, key cells in genesis and progression are T-lymphocytes, whose uncontrolled activation generates their migration towards the CNS attacking the myelin sheath in a specific manner. Since spironolactone affects specifically the activation of T-lymphocytes through blocking of interaction between the antigen-presenting cell and T-lymphocyte, spironolactone affects progression of MS mediated by T-lymphocytes and not systemic lupus erythematosus mediated by B-lymphocytes.

In conclusion, our studies show that the use of a spironolactone composition suppresses specifically the autoimmune damage associated with MS, through inhibition of the activation of T-lymphocytes, which can be translated in a new use of a spironolactone composition useful as immunomodulator, which would allow the benefit of population of patients suffering from this disease.

REFERENCES

1.—Atlas multiple sclerosis resources in the World, 2008. Geneva, World Health Organization. ISBN 978 92 4 156375 8.2.—Pericot, I &. X. Montalban. New drugs, mitoxantrone. Neurology, 2003. 18(6):318-323.
3.—Aharoni R., Herschkovitz A., Eilam R., Blumberg-Hazan M., Sela M., Bruck, W. and. Arnon R. Demyelination arrest and remyelination induced by glatiramer acetate treatment of experimental autoimmune encephalomyelitis. PNAS, 2008. 105(32): 11358-11363
4.—Skihara V., Silvaa C., Chojnackia A., Döringa A., Stallcupb W. B., Weissa S. and V. Wee Yonga. Promoting oligodendrogenesis and myelin repair using the multiple sclerosis medication glatiramer acetate. Proceeding of the National Academy of Sciences. 2009. 106(42): 17992-17997
5.—Goodin D S, Cohen B A, O'Connor P, Kappos L, Stevens J C. Assessment: the use of natalizumab (Tysabri) for the treatment of multiple sclerosis (an evidence-based review): report of the Therapeutics and Technology Assessment Subcommittee of the American Academy of Neurology. Neurology. 2008 Sep. 2; 71(10):766-73.
6.—Pitt B. et al. 1999. The effect of spironolactone on morbidity and mortality In patients with severe heart failure. The New England Journal of Medicine, 341(10): 709-7177.—IE20060891 A1 (Nov. 6, 2008) Spironolactone and analogues as modulators of chemokine receptor activity. Prendergast Patrick Thomas.
8.—Herrada A. A., Contreras F. J., Marini N. P., Amador C. A., González P. A., Cortés C. M., Riedel C. A., Carvajal C. A., Figueroa F., Michea L. F., Fardella C. E., and Kalergis A. M. Aldosterone Promotes Autoimmune Damage by Enhancing Th17-Mediated Immunity. The Journal of Immunology, 2010, 184, 191-202.
9.—Bolland S., Young-Sun Yim, Tus K., Wakeland E. K., and Ravetch J. V. Genetic Modifiers of Systemic Lupus Erythematosus in FcγRIIB−/− Mice. Journal of Experimental Medicine. 2002. vol. 195 no. 91167-1174.

The invention claimed is:

1. A method of treating multiple sclerosis, comprising administering to a patient in need thereof a pharmaceutical composition comprising a therapeutically effective amount of spironolactone or a polymorph, hydrate, or solvate thereof as the sole active ingredient and a pharmaceutically acceptable excipient, wherein the composition inhibits activation of T-lymphocytes in the patient, and wherein the method does not include administration of aldosterone to the patient.

2. The method of claim 1, wherein the pharmaceutical composition is orally administered to the patient.

3. The method of claim 2, wherein the pharmaceutical composition is a tablet, coated tablet, hard capsule, soft capsule or powder and comprises a dose of 25 to 400 mg of spironolactone or a polymorph, hydrate, or solvate thereof.

4. The method of claim 1, wherein the pharmaceutical composition is parenterally administered to the patient and comprises a dose of 25 to 400 mg of spironolactone or a polymorph, hydrate, or solvate thereof.

5. The method of claim 4, wherein the pharmaceutical composition is in the form of an injectable solution or suspension.

6. The method of claim 4, wherein administering comprises implanting a device in the patient that releases the pharmaceutical composition.

7. A method of treating multiple sclerosis, comprising obtaining T-cells and dendritic cells from peripheral blood of a patient suffering from multiple sclerosis, treating the T-cells and dendritic cells with a pharmaceutical composition comprising 2 to 10 µg/ml of spironolactone or a polymorph, hydrate, or solvate thereof as the sole active ingredient and a pharmaceutically acceptable excipient, and intravenously administering the treated T-cells and dendritic cells to the patient.

* * * * *